United States Patent
Ehlis et al.

[11] Patent Number: 6,111,103
[45] Date of Patent: Aug. 29, 2000

[54] DIRESORCINYL-ALKOXY- AND -ARYLOXY-S-TRIAZINES

[75] Inventors: Thomas Ehlis, Freiburg, Germany; Elek Borsos, Birsfelden, Switzerland; Helmut Luther; Bernd Herzog, both of Grenzach-Wyhlen, Germany

[73] Assignee: Ciba Specialty Chemicals Corporation, Tarrytown, N.Y.

[21] Appl. No.: 09/287,029

[22] Filed: Apr. 6, 1999

[30] Foreign Application Priority Data

Apr. 9, 1998  [EP]  European Pat. Off. .............. 98810314

[51] Int. Cl.$^7$ ................................................. C07D 251/22
[52] U.S. Cl. ............................................................. 544/219
[58] Field of Search ............................................. 544/219

[56] References Cited

U.S. PATENT DOCUMENTS

| | | | |
|---|---|---|---|
| 3,293,247 | 12/1966 | Duennenberger et al. | 260/248 |
| 5,298,030 | 3/1994 | Burdeska et al. | 544/219 |
| 5,364,749 | 11/1994 | Leppard et al. | 430/512 |
| 5,387,683 | 2/1995 | Burdeska et al. | 544/219 |

FOREIGN PATENT DOCUMENTS

| | | |
|---|---|---|
| 0 165 608 | 12/1985 | European Pat. Off. . |
| 5-025029 | 2/1993 | Japan . |

OTHER PUBLICATIONS

Chemical Abstracts, 118(24)240480e (for JP 05-25029 filed Jul. 22, 1991).
Koopman et al., Recueil, vol. 78, pp. 967-980, (1959).
Koopman, Recueil, vol. 80, pp. 158-172, (1961).
Brunetti et al., Helv. Chim. Acta, vol. 55(5), pp. 1566-95 (1972).

*Primary Examiner*—Richard L. Raymond
*Assistant Examiner*—Venkataraman Balasubramanian
*Attorney, Agent, or Firm*—Kevin T. Mansfield

[57] ABSTRACT

The invention relates to diresorcinyl-alkoxy- and -aryloxy-triazines of the formula

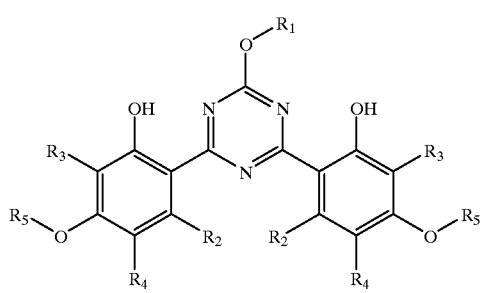

in which $R_1$ is $C_2$-$C_{30}$alkyl; $C_2$-$C_{30}$alkenyl; unsubstituted or $C_1$-$C_5$alkyl-mono- or polysubstituted $C_5$-$C_{12}$cycloalkyl, $C_1$-$C_5$alkoxy-$C_1$-$C_{12}$alkyl; amino-$C_1$-$C_{12}$alkyl; $C_1$-$C_5$monoalkylamino-$C_1$-$C_{12}$alkyl; $C_1$-$C_5$dialkylamino-$C_1$-$C_{12}$alkyl; a radical of the formula

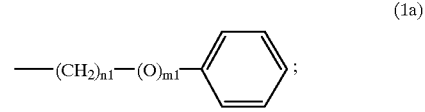 (1a)

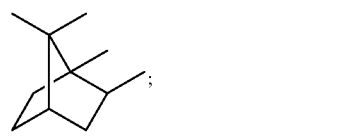

(1b)

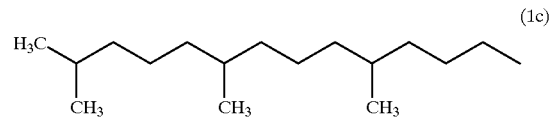

(1c)

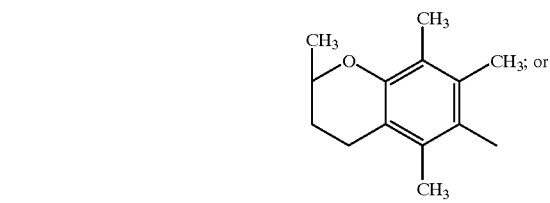

or (1d)

$R_2$, $R_3$ and $R_4$, independently of one another, are hydrogen, hydroxyl, $C_1$-$C_{30}$alkyl, $C_1$-$C_{30}$alkenyl, $R_5$ is hydrogen; or $C_1$-$C_5$alkyl;

$m_1$ is 0 or 1; and $n_1$ is 1 to 5.

The novel compounds are suitable as cosmetic UV-A absorbers.

6 Claims, No Drawings

DIRESORCINYL-ALKOXY- AND -ARYLOXY-S-TRIAZINES

The present invention relates to novel diresorcinyl-alkoxy- and -aryloxy-triazines, to a process for the preparation of these compounds and to their use in cosmetic compositions.

The novel diresorcinyl-alkoxy- and -aryloxy-triazines conform to the formula

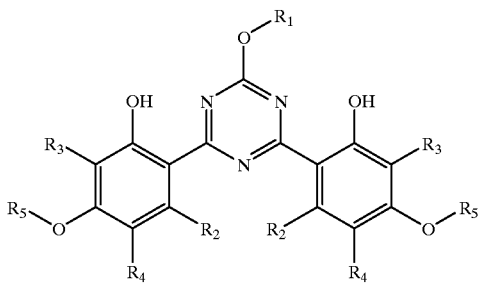

in which $R_1$ is $C_2$–$C_{30}$alkyl; $C_2$–$C_{30}$alkenyl; unsubstituted or $C_1$–$C_5$alkyl-mono- or polysubstituted $C_5$–$C_{12}$cycloalkyl, $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of the formula

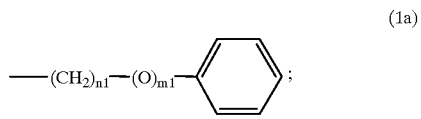
(1a)

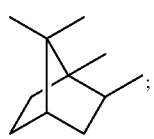
(1b)

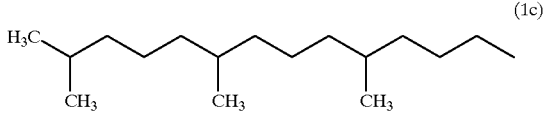
(1c)

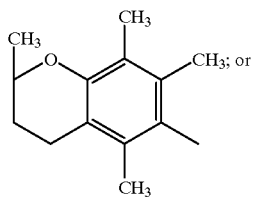
(1d)

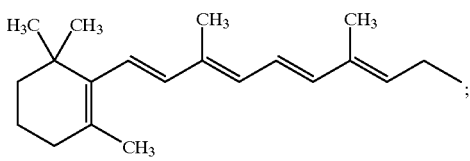

$R_2$, $R_3$ and $R_4$, in dependently of one another, are hydrogen, hydroxyl, $C_1$–$C_{30}$alkyl, $C_1$–$C_{30}$alkenyl, $R_5$ is hydrogen; or $C_1$–$C_5$alkyl;

$m_1$ is 0 or 1; and $n_1$ is 1 to 5.

Alkyl signifies a branched or unbranched hydrocarbon radical, for example methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methyihexyl, n-heptyl, isoheptyl, 1,1,3,3-tetramethylbutyl, 1-methylheptyl, 3-methylheptyl, n-octyl, iso-octyl; 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

Alkoxy radicals are straight-chain or branched radicals, for example methoxy, ethoxy, propoxy, butoxy or pentyloxy.

$C_5$–$C_{12}$cycloalkyl signifies, for example, cyclopentyl, cycloheptyl, cyclooctyl, cyclononyl, cyclodecyl, cycloundecyl, cyclodocecyl and, in particular, cyclohexyl.

Within the scope of the given meanings, alkenyl includes inter alia allyl, isopropenyl, 2-butenyl, 3-butenyl, isobutenyl, n-penta-2,4dienyl, 3-methyl-but-2-enyl, n-oct-2-enyl, n-dodec-2-enyl, isododecenyl, n-dodec-2-enyl, n-octadec-4-enyl or 3,7,11,11-tetramethyl-2,6,10-undecatrienyl.

Preference is given to compounds of the formula (1) in which $R_5$ is hydrogen.

Further preference is given to compounds of the formula (1) in which $R_1$ is $C_2$–$C_{30}$alkyl, in particular $C_4$–$C_{30}$alkyl and very particularly $C_6$–$C_{30}$alkyl.

Of these compounds, very particular preference is given to those in which $R_1$ is a 2-decylhexadecyl radical.

Other interesting compounds of the formula (1) are those in which $R_1$ is $C_4$–$C_{18}$alkyl radicals.

Of these compounds, very particular preference is given to those in which $R_1$ is an isooctadecyl radical, an n-octadecyl radical or a 2-hexyldecyl radical.

Particularly interesting compounds of the formula (1) are those in which $R_1$ is a $C_3$–$C_{12}$ radical, and in particular a 2-ethylhexyl radical.

Other illustrative representatives of the novel diresorcinyl-alkoxy- and-aryloxy-triazines are given in the table below:

TABLE 1
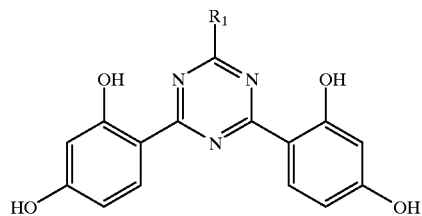
| Compound of the formula | $R_1$ |
|---|---|
| (3) | 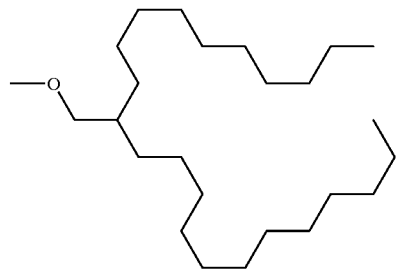 |
| (4) | —O-isoC$_{18}$H$_{38}$ |
| (5) | 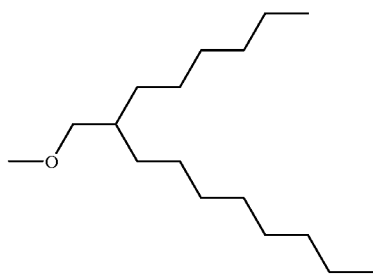 |
| (6) | —O-n-C$_{18}$H$_{37}$ |
| (7) | —O-2-ethylhexyl |
| (8) | 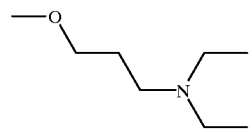 |
| (9) | 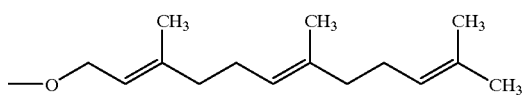 |
| (10) | 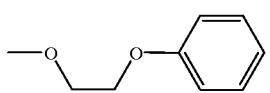 |
| (11) | 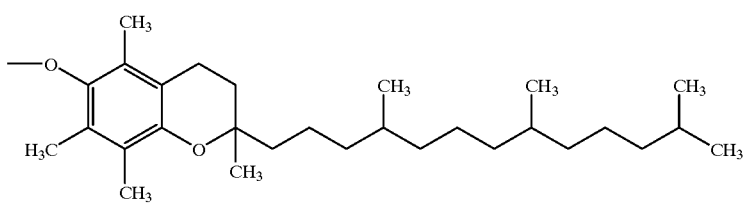 |

TABLE 1-continued
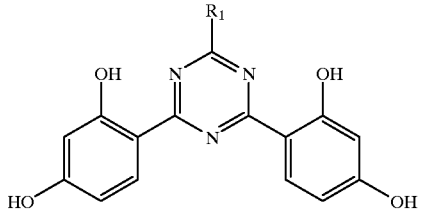
| Compound of the formula | R₁ |
|---|---|
| (12) | 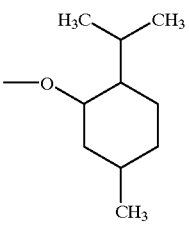 |
| (13) | 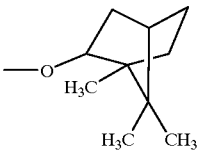 |
| (14) | 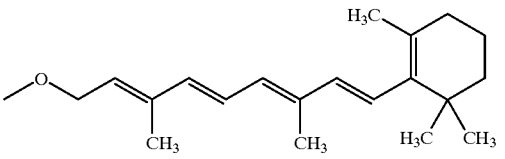 |
| (15) | 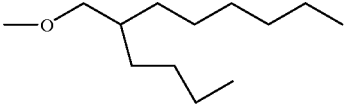 |
| (16) | 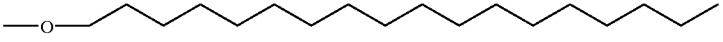 |
| (17) | 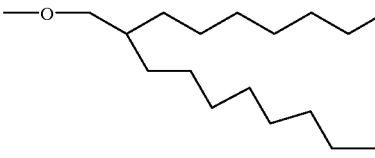 |
| (18) | 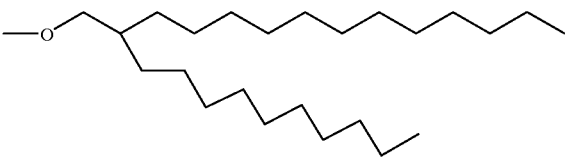 |
| (19) | 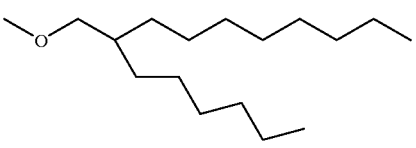 |

The novel diresorcinyl-alkoxy- and -aryloxy-triazines are prepared, for example, by reaction of cyanuric chloride with the alcohol $R_1$—OH to give the aryloxy- or alkoxy-dichloro-s-triazines respectively of the formula (2). In a Friedel-Crafts reaction, the novel compounds of the formula (1) are obtained in the second reaction stage. The reaction can be represented diagrammatically as follows:

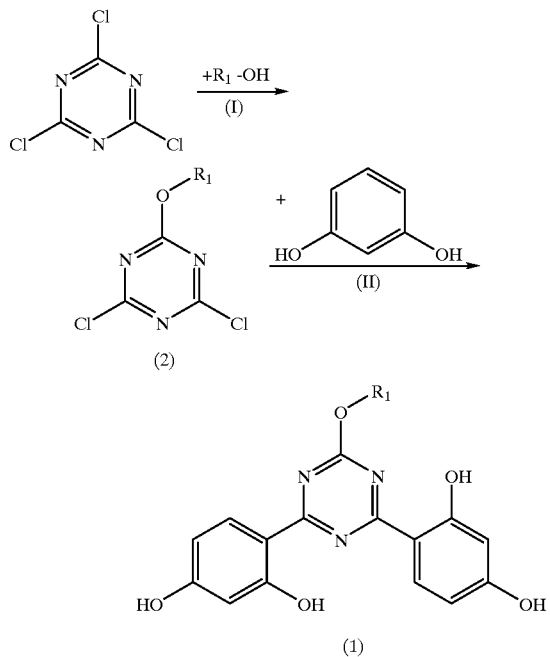

The first reaction stage is usually carried out in the presence of a solvent, for example acetone, methyl ethyl ketone, dimethylacetamide, toluene or xylene.

The temperatures here range from 0 to 130° C., in particular from 20 to 70° C.; the reaction times from 1 to 48 hours, preferably from 2 to 10 hours.

In the second reaction stage, the solvent normally used is toluene, nitrotoluene, nitrobenzene, anisole, xylene, benzene, sulfolane, chlorobenzene, dichlorobenzene, hydrocarbons (e.g. isooctane), chlorinated hydrocarbons, nitroalkanes, carbon disulfide, sulfur dioxide and mixtures of said solvents.

The temperatures here are from −10 to 200° C., in particular from 0 to 100° C.

The reaction times range from 1 to 100 hours, preferably from 2 to 50 hours.

The second reaction stage is normally carried out in the presence of a catalyst. Examples of suitable catalysts are: aluminium chloride, aluminium bromide, tin chloride, titanium tetrachloride, boron trifluoride and other Lewis acids.

The catalyst here is used in an amount of from 0.1 to 3 mol per mole of reactive chlorine.

In Friedel-Crafts reactions with dichloroalkoxy-s-triazines, dealkylations in the alkoxy radical are frequently observed. Under conditions according to the invention, i.e. control of the temperature; amount of catalyst, metered addition of the catalyst, the reaction proceeds particularly smoothly and without notable dialkylation.

Another method of synthesizing the novel diresorcinyl-alkoxy- and -aryloxy-triazines involves reacting cyanuric chloride with resorcinol to give the 2-chloro-4,6-resorcinyltriazine (compound of the formula (20) in the first reaction stage and reacting it with HO—$R_1$ to give the compound of the formula (1) in a second reaction stage, in accordance with the following equation:

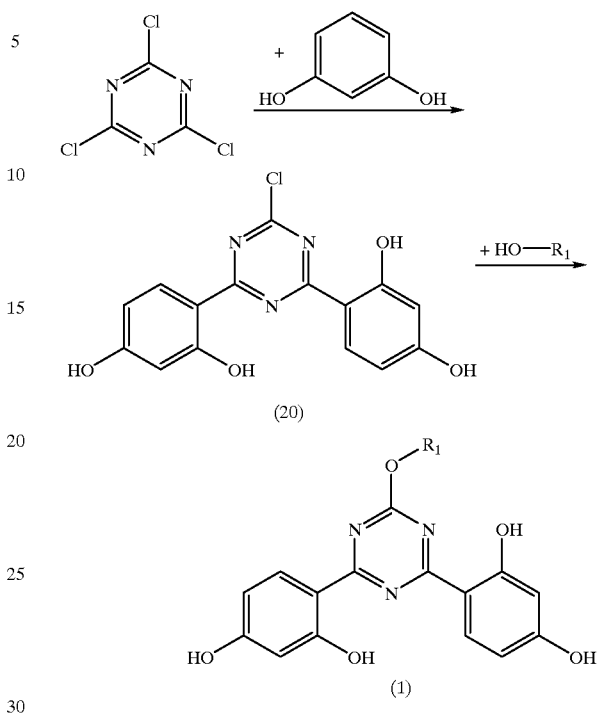

The p-hydroxyl groups of the resorcinyl radicals of the novel diresorcinyl-alkoxy- and -aryloxy-triazines of the formula (1) can, if desired, be further alkylated using suitable alkylating agents X—$R_5$ (X=Cl, Br, I, F) to give the corresponding alkoxy derivatives of the formula

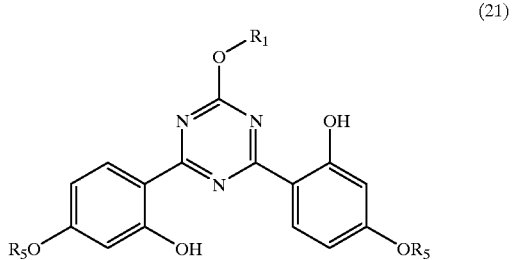

in which
$R_1$ and $R_5$ are defined as for formula (1).
Other suitable alkylating agents are epoxides, tosylates, dialkyl sulfates and alkyl glycidyl ethers.
The compounds of the formula

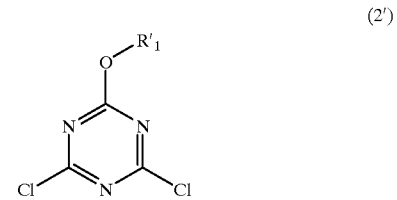

in which
$R_1$ is a branched $C_8$–$C_{20}$alkyl radical; a radical of the formula $m_1$ is 0 or 1; and $n'_1$ is 1 to 5, obtained in the first reaction stage are novel compounds. They are also provided by the invention.

The novel diresorcinyl-alkoxy- and -aryloxy-triazines of the formula (1) have an absorption maximum of ca. 350 nm, i.e. these compounds are UV-A absorbers. The compounds are therefore suitable in particular as UV filters, i.e. for protecting organic materials which are sensitive to ultraviolet light, in particular the skin and hair of humans and animals, from the harmful effects of UV radiation. These compounds are therefore suitable as light protection agents in cosmetic, pharmaceutical and veterinary medicine preparations. They can be used either in dissolved form or in the micronized state.

The present invention thus also relates to compounds of the formula (1) in micronized form, in which $R_1$ is $C_1$–$C_7$alkyl; $C_2$–$C_{30}$alkenyl; unsubstituted or $C_1$–$C_5$alkyl-mono- or polysubstituted $C_5$–$C_{12}$cycloalkyl; $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of the formula $R_2$, $R_3$ and $R_4$, independently of one another, are hydrogen, hydroxyl, $C_1$–$C_{30}$alkyl, $C_1$–$C_{30}$alkenyl, $R_5$ is hydrogen; or $C_1$–$C_5$alkyl;

$m_1$ is 0 or 1; and $n_1$ is 1 to 5.

If the novel UV absorbers are in micronized form, they usually have an average particle size of from 0.02 to 2 μm, preferably from 0.05 to 1.5 μm, very particularly from 0.1 to 1.0 μm. The methods for micronization are described, for example, in GB-A-2303549.

The grinding apparatus which can be used to prepare the novel micronized organic UV absorbers are, for example, a jet, ball, vibration or hammer mill, preferably a high-speed stirred mill. The grinding is preferably carried out using a grinding aid, for example an alkylated vinyl pyrrolidone polymer, a vinyl pyrrolidone-vinyl acetate copolymer, an acylglutamate or, in particular, a phospholipid.

Because of their lipophilicity, the compounds (1) can be easily incorporated into oil- and fat-containing cosmetic formulations particularly when $R_1$ is a branched alkyl radical having more than 8 carbon atoms.

The invention also provides a cosmetic preparation comprising at least one compound of the formula (1), and cosmetically compatible carriers or auxiliaries.

For cosmetic use, the novel light protection agents normally have an average particle size in the range from 0.02 to $2\mu$, preferably from 0.05 to $1.5\mu$, very particularly from 0.1 to $1.0\mu$. As mentioned above, the insoluble novel UV absorbers can be brought into the desired particle size by customary grinding methods. The grinding is preferably carried out in the presence of from 0.1 to 30% by weight, preferably from 0.5 to 15% by weight, based on the UV absorber, of a grinding aid.

In addition to the novel UV absorber, the cosmetic preparation can also comprise one or more further UV protective substances from the following classes of substance:

1. p-Aminobenzoic acid derivatives, for example 2-ethylhexyl 4-dimethylaminobenzoate;
2. Salicylic acid derivatives, for example 2-ethylhexyl salicylate;
3. Benzophenone derivatives, for example 2-hydroxy-4-methoxybenzophenone and its 5-sulfonic acid derivative;
4. Dibenzoylmethane derivatives, for example 1-(4-tert-butylphenyl)-3-(4-methoxyphenyl)propane-1,3-dione;
5. Diphenyl acrylates, for example 2-ethylhexyl 2-cyano-3,3-diphenyl acrylate and 3-(benzo-furanyl) 2-cyanoacrylate;
6. 3-Imidazol-4-yl-acrylic acid and 3-imidazol-4-yl acrylates;
7. Benzofuran derivatives, in particular 2-(p-aminophenyl)benzofuran derivatives, described in EP-A-582,189, U.S. Pat. No. 5,338,539, U.S. Pat. No. 5,518,713 and EP-A-613,893;
8. Polymeric UV absorbers, for example the benzylidene malonate derivatives described in EP-A-709,080;
9. Cinnamic acid derivatives, for example the 2-ethylhexyl or isoamyl 4-methoxycinnamate or cinnamic acid derivatives disclosed in U.S. Pat. No. 5,601,811 and WO 97/00851;
10. Camphor derivatives, for example 3-(4'-methyl)benzylidenebornan-2-one, 3-benzylidenebornan-2-one, N-[2(and 4)-2-oxyborn-3-ylidene-methyl)benzyl] acrylamide-polymer, 3-(4'-trimethylammonium)-benzylidenebornan-2-one methyl sulfate, 3,3'-(1,4-phenylenedimethine)bis(7,7-dimethyl-2-oxo-bicyclo-[2.2.1]heptane-1-methanesulfonic acid) and salts, 3-(4'-sulfo)benzylidenebornan-2-one and salts;
11. Trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517,104, EP-A-507,691, WO 93/17002 and EP-A-570,838;
12. 2-Hydroxyphenylbenzotriazole derivatives;
13. 2-Phenylbenzimidazole-5-sulfonic acid and salts thereof;
14. Menthyl o-aminobenzoate;
15. $TiO_2$ (with various coatings), ZnO and mica.

It is also possible to use the UV absorbers described in "Sunscreens", Eds. N. J. Lowe, N. A. Shaath, Marcel Dekker, Inc., New York and Basel or in Cosmetics & Toiletries (107), 50ff (1992) as additional UV protective substances in the novel formulation.

Furthermore, the novel cosmetic preparation can also be used together with known antioxidants, for example vitamin E, carotinoids or HALS (="Hindered Amine Light Stabilizers") compounds.

The novel cosmetic preparation comprises from 0.1 to 15% by weight, preferably from 0.5 to 10% by weight, based on the total weight of the composition, of a UV absorber or a mixture of UV absorbers and a cosmetically compatible auxiliary.

The cosmetic preparation can be prepared by physically mixing the UV absorber(s) with the auxiliary by customary methods, for example by simply stirring the individual components together.

The novel cosmetic preparation can be formulated as a water-in-oil or oil-in-water emulsion, as an oil-in-alcohol lotion, as a vesicular dispersion of an ionic or nonionic amphiphilic lipid, as a gel, as a solid stick or as an aerosol formulation.

As a water-in-oil or oil-in-water emulsion, the cosmetically compatible auxiliary preferably comprises from 5 to 50% of an oil phase, from 5 to 20% of an emulsifier and from 30 to 90% of water. The oil phase can comprise any oil suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the novel cosmetic preparation, it is possible to use any conventional emulsifier, for example one or more ethoxylated esters of natural derivatives, for example poly-ethoxylated esters of hydrogenated castor oil; or a silicone oil emulsifier, for example silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic preparation can also comprise other components, for example emollients, emulsion stabilizers, skin moisturizers, skin-tanning accelerators, thickeners, for example xanthan, humectants, for example glycerol, preservatives, fragrances and dyes.

The novel cosmetic preparation is notable for its excellent protection of the human skin from the harmful effects of sunlight.

The novel diresorcinyl-alkoxy- and -aryloxy-s-triazines are notable for high thermal stability and are thus used as stabilizers for organic polymers, in particular surface coatings, against their damage by light, oxygen and heat.

The material stabilized using the novel compounds is notable for excellent resistance to weathering and light effects, and excellent photostability of the incorporated stabilizer.

The materials to be stabilized can be, for example, oil, fats, waxes or biocides. Of particular interest is the use in polymeric materials, as are present in plastics, rubbers, paints, surface coatings, photographic material or adhesives.

The invention thus also provides a composition comprising (A) an organic material which is sensitive to damage by light, oxygen and/or heat, and (B) as stabilizer, a compound of the formula (1).

The invention also relates to a method of stabilizing organic material from damage by light, oxygen and/or heat, wherein a compound of the formula (1) is added as stabilizer to said material, and also to the use of the compound of the formula (1) for stabilizing organic material.

The amount of stabilizer to be used depends on the organic material to be stabilized and the intended use of the stabilized material. In general, the novel composition comprises, per 100 parts by weight of component (A), from 0.01 to 15 parts by weight, in particular from 0.05 to 10 parts by weight, and especially from 0.1 to 5 parts by weight of the stabilizer (component (B)).

The stabilizer (component (B)) can also be a mixture of two or more compounds of the formula (1). The novel compositions can, in addition to the novel compounds, also comprise other stabilizers or other additives, for example antioxidants, further light protection agents, metal deactivators, phosphites or phosphonites.

The type and amount of further stabilizers added is determined by the type of substrate to be stabilized and its intended use; frequently, from 0.1 to 5% by weight, based on the polymer to be stabilized, are used.

Incorporation into the organic polymers, for example into the synthetic organic, in particular thermoplastic, polymers, can take place by adding the novel triazine compounds and optionally further additives by methods customary in the art. Incorporation can expediently take place before or during shaping, for example by mixing the pulverulent components or by adding the stabilizer to the melt or solution of the polymer, or by applying the dissolved or dispersed compounds onto the polymer, if necessary with subsequent evaporation of the solvent. In the case of elastomers, these can also be stabilized as latices. Another possible way of incorporating the novel mixtures into polymers involves adding them before or during polymerization of the corresponding monomers or before crosslinking.

The stabilized polymer compositions obtained in this way can be converted into shaped articles, for example fibres, films, tapes, sheets, multi-wool sheets, containers, tubes and other profiles, by conventional methods, for example by hot pressing, spinning, extrusion or injection moulding.

The polymers stabilized in this way are notable for high weathering resistance, especially for high resistance to UV light. They thus retain their mechanical properties and their colour and gloss even when used outdoors for a long period.

In the following examples, percentages are by weight. The amounts in the case of the diresorcinyl triazine compounds used refer to the pure substance.

PREPARATION EXAMPLES

Example 1a
Preparation of the Compound of the Formula

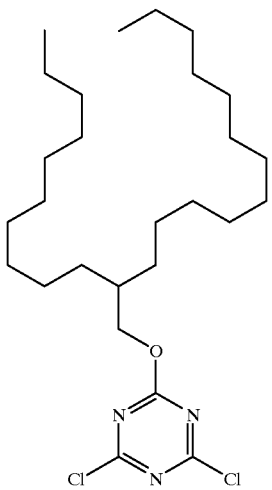

(101a)

Cyanuric chloride (9.22 g, 0.05 mol) is introduced into toluene (80 ml). Over the course of 40 min a mixture of 2-decyl-1-tetradecanol (20.1 g, 0.057 mol), dimethylacetamide (6.53 g, 0.075 mol) and toluene (20 ml) is added dropwise at 30–55° C. The mixture is then stirred at 50° C. for 4 h and filtered over kieselguhr.

The filtrate is extracted by shaking with tert-butyl methyl ketone (50 ml) and ice-cold 10% NaCl solution (150 ml). The organic phase is washed again using 10% NaCl solution, separated off and dried over $Na_2SO_4$. After the solvent has been stripped off, the oil obtained is worked up by column chromatography (silica gel, toluene/hexane 7:3).

This gives a colourless oil of the compound of the formula (101a).

Yield:18.4 g (73%). $^{13}$C NMR (90 MHz, $CDCl_3$. TMS): δ=14.50; 23.09; 27.08; 29.74; 29.76; 29.97; 30.04; 30.26; 30.32; 31.31; 32.32; 37.75; 73.68; 171.63; 172.84.

Elemental Analysis:

|  | % C | % H | % N |
|---|---|---|---|
| Calculated: | 64.52 | 9.83 | 8.36 |
| Found: | 65.0 | 9.9 | 8.2 |

Example 1b
Preparation of the Compound of the Formula (101)

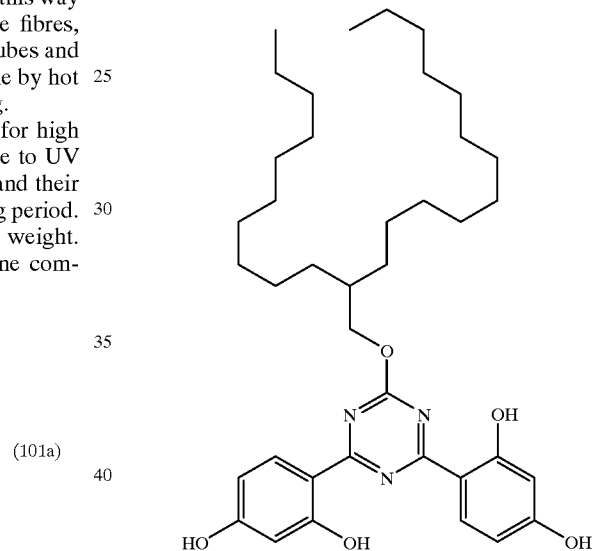

(101)

Resorcinol (4.9 g, 0.045 mol) is introduced into nitrobenzene (40 ml). At 10–15° C., powdered aluminium chloride (5.9 g, 0.044 mol) is introduced in portions. The mixture is then stirred for 30 min, the compound of the formula (101a) (10.05 g, 0.020 mol) dissolved in nitrobenzene (10 ml) is added dropwise over the course of 30 min at 10–15° C., and the mixture is then stirred for 5 hours. The mixture is then stirred for a further 3 hours at room temperature. The reaction can be monitored using thin-layer chromatography (silica gel, toluene/acetone 9:1).

The reaction mixture is poured, while stirring, into a mixture of iced water (100 ml) and 2N-HCl (25 ml). A precipitate settles out. Nitrobenzene residues are removed by steam distillation. The solid residue is dissolved in acetone, dried using $Na_2SO_4$, concentrated by evaporation and separated by column chromatography (silica gel, toluene/ethyl acetate 8:2). This gives 5.7 g of a yellow powder which, after recrystallization from hexane/dioxane 6:4, is produced in analysis-grade quality.

This gives pale yellow crystals of the compound of the formula (101).

Yield: 4.1 g (31%); m.p.: 165–166° C. UV/Vis (EtOH): $\lambda_{max}$ (ε)=350 (34482) nm; $^{13}$C NMR (90 MHz, $D_6$-DMSO, TMS): δ=14.6 (CH₃); 23.0 (CH₂); 27.0 (CH₂); 29.8 (CH₂); 30.0 (CH₂); 30.06 (CH₂); 30.11 (CH₂); 30.3 (CH₂); 31.3 (CH₂); 32.3 (CH₂); 37.6 (CH); 71.2 (CH₂O);103.8 (CH); 109.0 (CH); 109.4 (CH); 131.6 (CH); 164.6 (C$_q$); 65.1 (C$_q$); 67.8 (C$_q$); 171.5 (C$_q$).

Elemental Analysis:

|  | % C | % H | % N |
|---|---|---|---|
| Calculated: | 72.08 | 9.15 | 6.47 |
| Found: | 72.04 | 9.16 | 6.48 |

Example 2a

Preparation of the Compound of the Formula (102a):

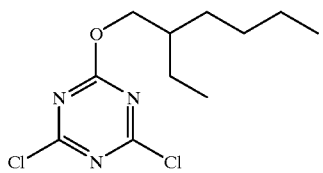
(102a)

The compound of the formula (102a) is prepared in an analogous manner to the compound (101a) from Example 1. The alcohol component used is 2-ethylhexanol. The crude product which is obtained as a liquid is purified by distillation under a high vacuum (b.p. 118–119° C./0.2 torr).

The crude product can also be purified by column chromatography on silica gel (toluene/hexane 9:1).

The compound has already been described in U.S. Pat. No. 3,542,752 (American Cyanamid).

Example 2b

Preparation of the Compound of the Formula (102):

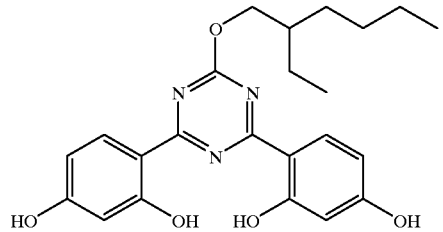
(102)

The compound of the formula (102a) (11.1 g, 0.040 mol), resorcinol (9.7 g, 0.088 mol), xylene (80 ml) and sulfolane (30 ml) are introduced initially. At 35–40° C., pulverized aluminium chloride (11.7 g, 0.088 mol) is introduced over the course of 20 min, and the mixture is then stirred for 5 hours. The two-phase reaction mixture is separated. The lower orange-red phase is allowed to flow into a mixture of iced water (250 ml) and 32% hydrochloric acid (20 ml). The solid which separates out is filtered off, washed with acetone and dried. It is recrystallized several times from dioxane.

This gives pale yellow crystals of the compound of the formula (102).

| Solubility in ethanol (25° C.): 1.50% | |
|---|---|
| m.p. | 235–236° C. |
| Yield: | 5 g (29%) |
| UV/Vis (EtOH): | λ$_{max}$ (ε) = 350 (39177) nm |

¹³C NMR (90 MHz, D₆-DMSO, TMS): β=11.6 (CH₃); 14.7 (CH₃); 23.3 (CH₂); 24.0 (CH₂) 29.3 (CH₂); 30.6 (CH₂); 38.9 (CH); 71.0 (CH2O); 103.9 (CH); 109.5 (CH); 131.9 (CH); 164.4 (C$_q$); 165.1 (C$_q$); 167.9 (C$_q$); 171.5 (C$_q$).

Elemental Analysis:

|  | % C | % H | % N |
|---|---|---|---|
| Calculated: | 64.93 | 6.40 | 9.88 |
| Found: | 64.6 | 6.4 | 9.9 |

Example 3a

Preparation of the Compound of the Formula (103a)

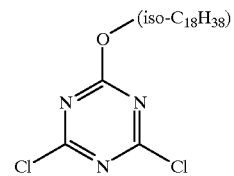
(103a)

The compound of the formula (103a) is prepared in an analogous manner to the compound (101a) from Example 1. The alcohol component used is an isooctadecanol isomer mixture (CA Reg.No. 27458-93-1).

Example 3b

Preparation of the Compound of the Formula (103):

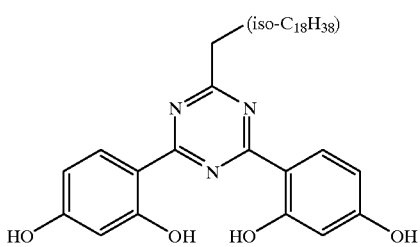
(103)

Resorcinol (6.6 g, 0.060 mol), nitrobenzene (40 ml) and a xylene isomer mixture (20 ml) are introduced initially. At 45–50° C., powdered aluminium chloride (7.0 g, 0.052 mol) is introduced and the mixture is stirred for 30 min. Then, at 0–5° C., over the course of 1.5 hours, a mixture of the compound of the formula (103a) (10.5 g, 0.025 mol) and xylene (10 ml) are added dropwise, and the mixture is then stirred for 5 hours at 2–3° C.

For work-up, the reaction mixture is allowed to run into a mixture of iced water (100 ml) and 2N HCl (25 ml). Nitrobenzene is removed by steam distillation. Butyl methyl ether (200 ml) is used to extract the crude product from the residue. The organic phase is washed with 5% NaCl solution, dried and freed from solvent. Column chromatography (silica gel, toluene/acetone 9:1) is then used to separate the mixture.

This gives beige-coloured crystals of the compound of the formula (103).

Yield: 4.6 g (32%); m.p.: 166–167° C.; UV/Vis (EtOH): $\lambda_{max}$=351 nm $^{13}$C NMR (90 MHz, $D_6$-DMSO, TMS): δ=13.9 ($CH_3$); 22.1 ($CH_2$); 26.1 ($CH_2$); 28.77 ($CH_2$); 28.82 ($CH_2$); 29.0 ($CH_2$); 29.1 ($CH_2$); 29.4 ($CH_2$); 30.6 ($CH_2$); 31.3 ($CH_2$); 31.4 ($CH_2$); 36.7 (CH); 70.5 ($CH_2O$); 103.1 (CH); 108.4 (CH); 108.7 (CH); 131.0 (CH); 163.4 ($C_q$); 164,4 ($C_q$); 167.2 ($C_q$); 170.8 ($C_q$).

Elemental Analysis:

|  | % C | % H | % N |
|---|---|---|---|
| Calculated: | 70.06 | 8.37 | 7.43 |
| Found: | 70.2 | 8.5 | 7.3 |

Example 4a

Preparation of the Compound of the Formula (104a)

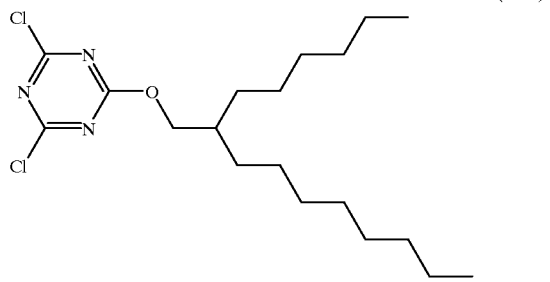

(104a)

The compound of the formula (104a) is prepared in an analogous manner to the compound of the formula (100a) from Example 1. The alcohol component used is 2-hexyldecanol.

Example 4b

Preparation of the Compound of the Formula (104)

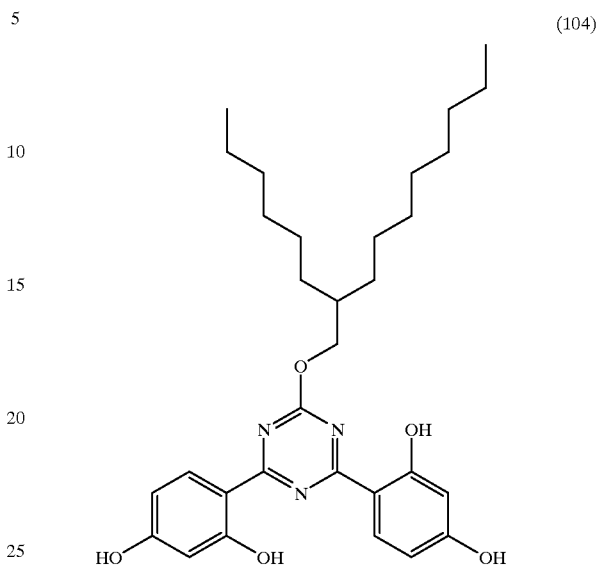

(104)

Resorcinol (6.6 g, 0.060 mol) is introduced into a solution of the compound of the formula (104a) (9.76 g, 0.025 mol) in toluene (80 ml) at 0–5° C. over the course of 30 min. Pulverized aluminium chloride (7.0 g, 0.025 mol) is then introduced into the reaction mixture in small portions at 2° C. over the course of 30 min, and then the mixture is stirred for 4 hours. The cold bath is removed and the mixture is then stirred overnight at room temperature. The reaction can be monitored by thin-layer chromatography (silica gel, toluene/acetone 9:1).

Pouring the reaction mixture into dilute hydrochloric acid (150 ml of $H_2O$+25ml of conc. HCl) results, at 50° C., in phase separation. The toluene is removed from the upper organic phase by steam distillation. The solid which has separated off is extracted with tert-butyl methyl ether. The extract, dried over $Na_2SO_4$, is concentrated by evaporation and separated by column chromatography (silica gel, toluene/acetone 8:2).

This gives pale yellow crystals of the compound of the formula (104) (from dioxane/hexane).

Yield: 10.1 g (74.8%); m.p. 175–176° C.; UV/Vis (EtOH.): $\lambda_{max}$ (ε)=351 (36148) nm; $^{13}$C NMR (90 MHz, $D_6$-DMSO, TMS): δ=14.7 ($CH_3$); 23.0 ($CH_2$); 26.9 ($CH_2$); 27.0 ($CH_2$); 29.6 ($CH_2$); 29.8 ($CH_2$); 29.9 ($CH_2$); 30.2 ($CH_2$); 31.4 ($CH_2$); 31.5 ($CH_2$); 32.2 ($CH_2$); 37.6 (CH); 71.3 ($CH_2O$); 103.9 (CH); 109.2 (CH); 109.5 (CH); 131.9 (CH); 164.5 ($C_q$); 165.1 ($C_q$); 168.0 ($C_q$); 171.6 ($C_q$)

Elemental Analysis:

|  | % C | % H | % N |
|---|---|---|---|
| Calculated: | 69.25 | 8.06 | 7.81 |
| Found: | 69.1 | 7.9 | 7.8 |

Example 5a
Preparation of the Compound of the Formula (105a)

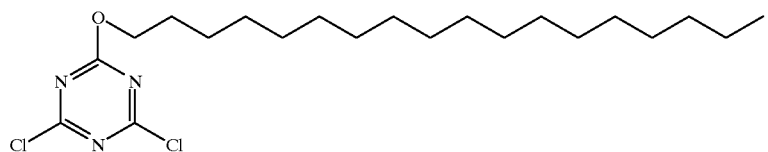

The compound of the formula (105a) is prepared in an analogous manner to the compound of the formula (101a). The alcohol component used is 1-octadecanol.

Example 5b
Preparation of the Compound of the Formula (105):

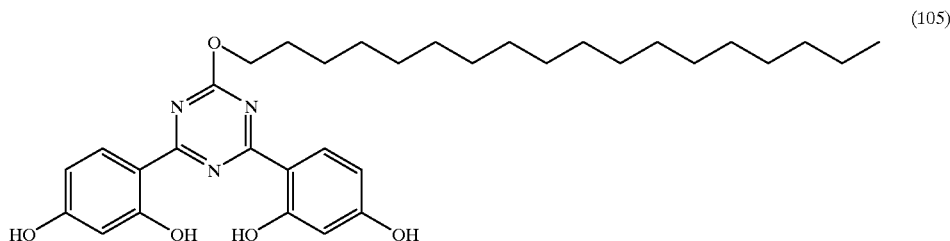

(105)

Nitrobenzene (40 ml), resorcinol (6.6 g, 0.06 mol) and a xylene isomer mixture (20 ml) are introduced initially at room temperature. At 45–50° C., pulverized aluminium chloride (7.0 g, 0.05 mol) is introduced and the mixture is then stirred at 45–50° C. for 30 min. Then, at 0–5° C., a solution of the compound of the formula (108a) (10.5 g, 0.025 mol) in a xylene isomer mixture (15 ml) is added dropwise over the course of 35 min. The mixture is then stirred for 3 hours at 0–5° C. and then for 1.5 hours at 5–10° C. The reaction suspension is stirred into a mixture of iced water (200 ml) and 4 N hydrochloric acid (25 ml) and heated to 50° C. Extraction with tert-butyl methyl ether (200 ml) is then carried out and the organic phase is concentrated by evaporation on a rotary evaporator. Water is added to the residue, and residues of the nitrobenzene/xylene isomer mixture are removed by steam distillation. The crude product is recrystallized from dioxane/acetone 6:4.

The reaction can be monitored by thin-layer chromatography (silica gel, toluene/acetone 9:1).

This gives pale yellow crystals.

Yield: 6.9 g (48.8%); m.p.:213–214° C.; UV/Vis (EtOH): $\lambda$max ($\epsilon$)=350 (31662) nm Elemental Analysis:

|  | % C | % H | % N |
|---|---|---|---|
| Calculated: | 70.06 | 8.37 | 7.43 |
| Found: | 70.4 | 8.6 | 7.5 |

Example 6a
Preparation of the Compound of the Formula (106a)

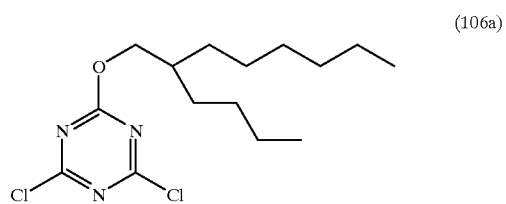

(106a)

The compound of the formula (106a) is prepared in an analogous manner to the compound of the formula (101a). The alcohol component used is 2-butyl-1-octanol.

Example 6b
Preparation of the Compound of the Formula (106)

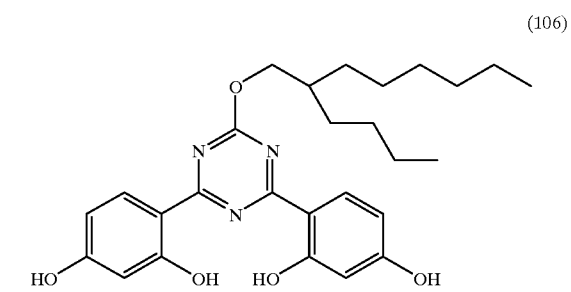

(106)

The compound of the formula (106a) (16.7 g, 0.05 mol), toluene (150 ml) and resorcinol (13.2 g, 0.12 mol) are introduced initially at room temperature. At 0–5° C., pulverized aluminium chloride (14.7 g, 0.11 mol) is introduced in small portions over the course of 1 h 15 min and the mixture is then stirred at 0–5° C. for 6.5 hours. 2N HCl (60 ml) is then added dropwise to the reaction mixture with cooling. The yellow emulsion is extracted with butyl methyl ether. The organic phase is washed with 10% NaCl solution, dried over $Na_2SO_4$ and freed from the solvent. The solid residue is purified by column chromatography (silica gel, toluene/butyl methyl ether 75:25).

The reaction can be monitored by thin-layer chromatography (silica gel, toluene/acetone 9:1).

This gives beige crystals.

Yield: 7.0 g (29.1%); m.p.: 170–172° C.; $^{13}$C NMR (90 MHz, $D_6$DMSO, TMS): δ=14.7; 23.0; 23.3; 27.0; 29.3; 29.9; 31.2; 31.5; 32.1; 37.5; 67.2; 103.9; 109.2; 109.5; 131.6; 164.5 ($C_q$); 165.1 ($C_q$); 168.0 ($C_q$); 171.6 ($C_q$).
Elemental Analysis:

|  | % C | % H | % N |
|---|---|---|---|
| Calculated: | 67.34 | 7.33 | 8.73 |
| Found | 67.3 | 7.4 | 8.5 |

Example 7a
Preparation of the Compound of the Formula (107a)

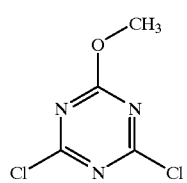
(107a)

The compound of the formula (107a) is prepared in an analogous manner to the compound of the formula (101a). The alcohol component used is methanol.

Example 7b
Preparation of the Compound of the Formula (107)

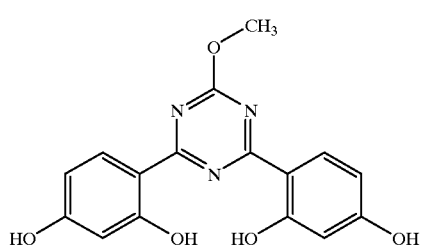
(107)

The compound of the formula (107a) is prepared according to the method described for the compound of formula (105). The solid which has separated off is stirred in warm methanol (150 ml), filtered off with suction, washed with methanol, dried and recrystallized from acetonitrile/N-methyl-2-pyrrolidone. The resulting crystalline powder is extracted with boiling methanol in order to remove included N-methyl-2-pyrrolidone, filtered off and dried. The reaction can be monitored by thin-layer chromatography (silica gel, toluene/acetone 8:2).

This gives pale yellow crystals.

The compound is disclosed in EP-A-0,165,608.

Solubility in ethanol (25° C.): 0.08%; Yield: 10.8 g (66.0%); m.p.: >300° C.; UV/Vis (EtOH): $\lambda_{max}$ (ε)=350 (36949) nm; $^{13}$C NMR (90 MHz, $D_6$-DMSO, TMS): δ=53.9 ($OCH_3$); 102.0 (CH); 107.6(CH); 130.0(CH); 107.3 ($C_q$); 162.5 ($C_q$); 163.2 ($C_q$); 166.2 ($C_q$); 169.5 ($C_q$).
Elemental Analysis:

|  | % C | % H | % N |
|---|---|---|---|
| Calculated: | 58.72 | 4.00 | 12.84 |
| Found: | 58.64 | 4.18 | 12.76 |

Example 8a
Preparation of the Compound of the Formula (108a)

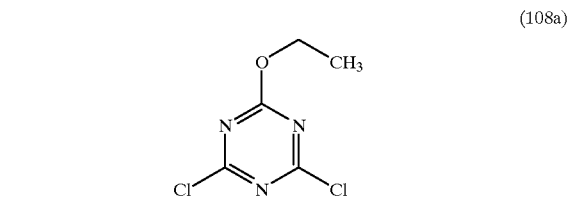
(108a)

The compound of the formula (108a) is prepared in an analogous manner to the compound of the formula (101a). The alcohol component used is ethanol.

Example 8b
Preparation of the Compound of the Formula (108)

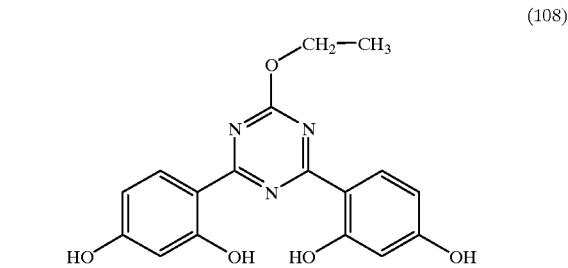
(108)

The compound of the formula (108) is prepared according to the compound of formula (105).

The reaction can be monitored using thin-layer chromatography (silica gel, toluene/acetone 8:2).

This gives pale beige crystals.

Solubility in ethanol (25° C.): 0.17%; Yield: 3.6 g (42.2%); m.p.:>300° C.; UV/Vis (EtOH): $\lambda_{max}$ (ε)=350 (36761) nm; $^{13}$C NMR (90 MHz, $D_6$-DMSO, TMS): δ=14.8 ($CH_3$); 64.9 ($CH_2$); 103.8 (CH); 109.5 (CH); 131.8 (CH); 109.1 ($C_q$); 164.4 ($C_q$); 165.0 ($C_q$); 167.5 ($C_q$); 171.4 ($C_q$).

Example 9a
Preparation of the Compound of the Formula (109a):

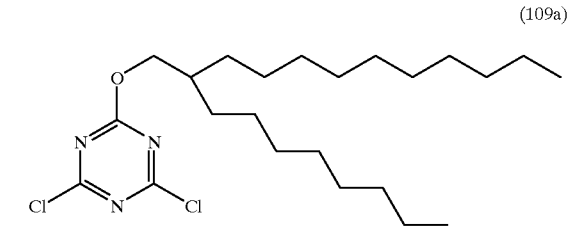
(109a)

The compound of the formula (109a) is prepared in an analogous method to the compound of the formula (101a). The alcohol component used is 2-octyl-1-dodecanol.

Example 9b
Preparation of the Compound of the Formula (109):

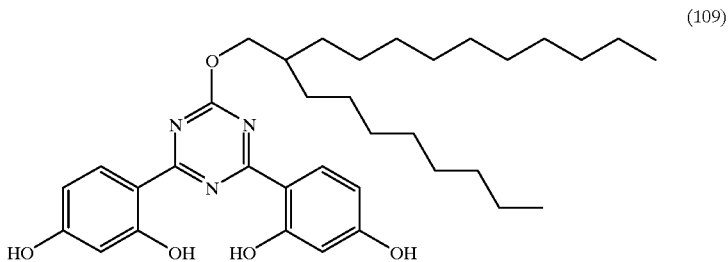

(109)

Resorcinol (13.2 g, 0.12 mol) is introduced into nitrobenzene (30 ml). At 50–60° C., a solution of the compound of the formula (109a) (22.3 g, 0.05 mol) in toluene (70 ml) is added. At 0–5° C., pulverized aluminium chloride (14.7 g, 0.11 mol) is introduced over the course of 40 min and the mixture is then stirred for 6 hours at 0–5° C. The reaction mixture is then stirred into 2N HCl, and the nitrobenzene is stripped off by steam distillation. The solid residue is separated off and extracted with butyl methyl ether. The organic phase is washed with 10% NaCl solution and 2% $Na_2CO_3$ solution, dried over $Na_2CO_4$ and evaporated. The crude product is purified by column chromatography (silica gel, toluene/acetone 85:15). Analytical-grade quality product is obtained by subsequent recrystallization from acetone.

The reaction can be monitored by thin-layer chromatography (silica gel, toluene/acetone 9:1).

This gives pale yellow crystals.

Yield: 7.1 g (23.9%); m.p.: 166–167° C.; $^{13}$C NMR (90 MHz, $D_6$-DMSO, TMS): δ=14.6; 23.0; 27.0; 29.6; 29.7; 29.9; 28.0; 30.2; 30.3; 31.4; 32.2; 37.6; 71.2; 103.9; 109.1; 109.5; 131.8; 164.5 ($C_q$); 165.1 ($C_q$); 168.0 ($C_q$); 171.6 ($C_q$).

Elemental Analysis:

|  | % C | % H | % N |
|---|---|---|---|
| Calculated: | 70.79 | 8.66 | 7.08 |
| Found: | 70.8 | 8.5 | 6.9 |

Example 10
Preparation of the Compound of the Formula (110):

The compound of the formula (101) (9.8 g, 0.015 mol), acetone (85 ml), water (40 ml) and 2N NaOH (15.8 ml) are introduced initially at room temperature. At 40° C., dimethyl sulfate (4.16 g, 0.04 mol) is added dropwise and the mixture is then stirred for 2.5 hours at 40° C. 1N HCl is used to adjust the pH to 6, and the solid is filtered off. The filter cake is dissolved in toluene, extracted by shaking with $H_2O$, dried and freed from the solvent. Separation by column chromatography (silica gel, toluene) and recrystallization from diethyl ether are then carried out. The reaction can be monitored using thin-layer chromatography (silica gel, toluene/acetone 95:5).

This gives pale beige crystals.

Yield: 3.1 g (30.5%); m.p.: 79–80° C.; UV/Vis (Dioxan): $\lambda_{max}$ (ε)=347 (36219) nm; $^{13}$C NMR (90 MHz, $CDCl_3$, TMS): δ=15.5; 24.1; 28.2; 30.8; 31.1; 31.4; 32.5; 33.3; 38.9; 56.9 ($OCH_3$); 72.7; 102.7; 109.4; 111.2 ($COCH_3$); 132.4; 165.9 ($C_q$); 167.1 ($C_q$); 168.8 ($C_q$); 172.8 ($C_q$).

Elemental Analysis:

|  | % C | % H | % N |
|---|---|---|---|
| Calculated | 72.64 | 9.37 | 6.20 |
| Found: | 72.77 | 9.39 | 6.20 |

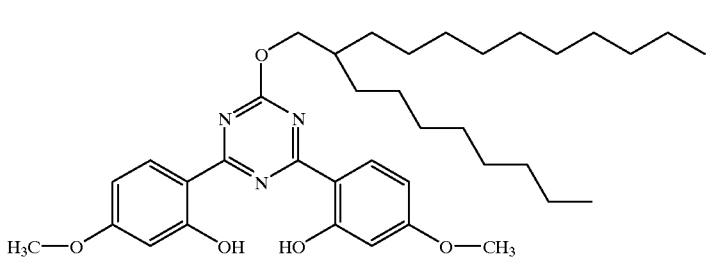

(110)

Example 11
Preparation of the Compound of the Formula (111):

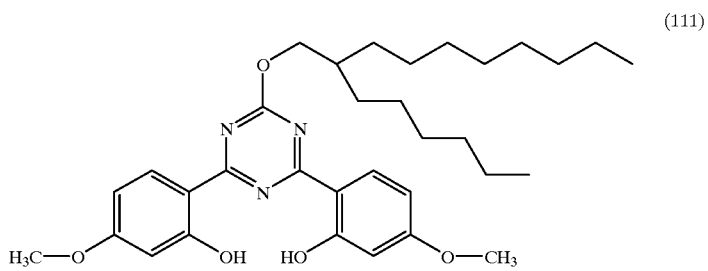

(111)

The compound of the formula (104) (10.8 g, 0.02 mol) is introduced into dioxane (100 ml). At 40° C., 2N NaOH (21 ml) is added and the mixture is then stirred for 15 min. Dimethyl sulfate (4.2 ml) is then metered in at 40° C. and the mixture is stirred for 5 hours. The solvent is stripped off using a rotary evaporator, and the residue is dissolved in toluene. The organic phase is extracted by shaking with 10% NaCl solution and dried. Pure product is obtained by separation by column chromatography (silica gel, toluene/acetone 98.5:1.5) and subsequent recrystallization from hexane.

The reaction can be monitored using thin-layer chromatography (silica gel, toluene/acetone 9:1).

This gives pale beige crystals.

Yield: 7.5 g (66.3%); m.p.: 99–100° C.; UV/Vis (EtOH): $\lambda_{max}$ ($\epsilon$)=348 (34123) nm; $^{13}$C NMR (90 MHz, CDCl$_3$, TMS): $\delta$=14.5; 23.1; 27.20; 27.21; 29.8; 30.0; 30.1; 30.4; 31.5; 32.27; 32.31; 38.9; 55.8 (OCH3); 71.7; 101.6; 108.4; 110.2; 131.2; 164.9 ($C_q$); 166.0 ($C_q$); 167.8 ($C_q$); 172.0 ($C_q$).

Elemental Analysis:

|  | % C | % H | % N |
|---|---|---|---|
| Calculated: | 70.06 | 8.37 | 7.43 |
| Found: | 70.0 | 8.4 | 7.1 |

Example 12
Preparation of the Compound of the Formula (112):

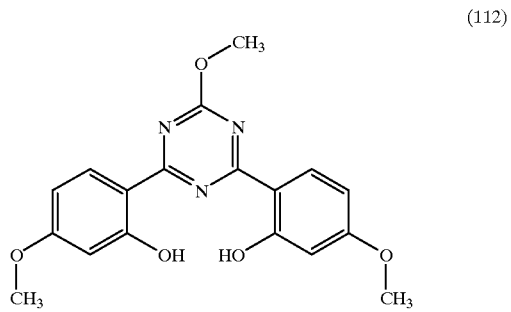

(112)

The compound of the formula (112) is prepared in an analogous manner to the compound of the formula (110). The solvent used is dioxane. The filtration product is washed with dioxane/H$_2$O and methanol and dried. It is then recrystallized from methyl cellosolve.

This gives pale yellow crystals.

Yield: 5.7 g (64.2%); m.p.: 193–194° C.; UV/Vis (Dioxan): $\lambda_{max}$ ($\epsilon$)=347 (37680) nm;

Application Examples

Example 13

Micronization 50 g of compound of the formula (108) are ground together with 7% of alkyl polyglycoside, 43% of H$_2$O and 80 g of zirconium sand until a particle size of $d_{50}$=150 nm is reached. The grinding sand is then separated off from the suspension, which comprises micronized compound of the formula (108).

Example 14

Sunscreen Formulation (W/O)

| | Components | % by weight |
|---|---|---|
| Oil phase | PEG-30 dipolyhydroxystearate (Arlacel P 135 ®) | 3.00 |
| | PEG-22/ dodecyl glycol copolymer (Elfacos ST 37 ®) | 1.00 |
| | Microcrystalline wax | 1.00 |
| | Hydrogenated castor oil | 0.50 |
| | Magnesium stearate | 1.00 |
| | Octyl stearate | 15.00 |
| | Coco glycerides | 2.00 |
| | Mineral oil | 3.00 |
| | Phenoxyethanol & parabens | 1.00 |
| | Octyl methoxycinnamate | 5.00 |
| | Dimethicone | 0.10 |
| Aqueous phase | Deionized water | 52.40 |
| | Magnesium sulfate (MgSO$_4$ × 7 H$_2$O) | 1.00 |
| | Propylene glycol | 4.00 |
| | 50% suspension corresponding to Example 13 | 10.00 |

Preparation Instructions:

The oil and the aqueous phase are heated separately to 80° C. and mixed together, and the mixture is vigorously homogenized. The mixture is then allowed to cool to 40° C. with gentle stirring. The 50% suspension of the micronized UV absorber of the formula (108) is added in portions with stirring, and stirring is continued for a further 15 minutes.

SPF (in vivo)=16 (COLIPA) [without micronized compound of the formula (108): SPF=6].

Example 15

Sunscreen Emulsion (O/W)

|   | Components | % by weight |
|---|---|---|
| A | Polyglyceryl-3 methylglucose distearate (Tego ® Care 450) | 2.0 |
|   | Decyl oleate | 5.7 |
|   | Isopropyl palmitate | 5.0 |
|   | Caprylic/capric triglyceride | 6.5 |
|   | Compound of the formula (101) | 3.5 |
| B | Glycerol | 3.0 |
|   | Phenonip | 0.5 |
|   | Deionized water | 72.4 |
| C | Carbomer 141 | 0.2 |
|   | Isopropyl palmitate | 0.8 |
| D | NaOH (10%) | 0.4 |

Preparation Procedure:

Phases A and B are heated separately to 80° C. and then mixed with gentle stirring. C is added to the mixture of A and B and then vigorously homogenized. The homogenate is allowed to cool to room temperature with gentle stirring. If necessary, the pH is adjusted by adding D.

SPF (in vitro)=3.0 (Optometrics SPF 290 Analyser, 2 $\mu$l/cm$^2$ on Transpore®-Tape) Australian/New Zealand Standard, 15/NZS 2604: 1993 (less than 10% transmission between 320 nm and 360 nm) is satisfied.

Example 16

Sunscreen Emulsion (O/W)

|   | Components | % by weight |
|---|---|---|
| A | Polyglyceryl-3 methylglucose distearate (Tego ® Care 450) | 2.0 |
|   | Decyl oleate | 5.7 |
|   | Isopropyl palmitate | 5.0 |
|   | Caprylic/capric triglyceride | 6.5 |
|   | Compound of the formula (101) | 3.0 |
|   | Octyl methoxycinnamate | 5.0 |
| B | Glycerol | 3.0 |
|   | Phenonip | 0.5 |
|   | Deionized water | 67.9 |
| C | Carbomer 141 | 0.2 |
|   | Isopropyl palmitate | 0.8 |
| D | NaOH (10%) | 0.4 |

Preparation Procedure:

Phases A and B are heated separately to 80° C. and then mixed with gentle stirring. C is added to the mixture of A and B and then vigorously homogenized. The homogenate is allowed to cool to room temperature with gentle stirring. If necessary, the pH is adjusted by adding D.

SPF (in vitro)=11.0 (Optometrics SPF 290 Analyser, 2 $\mu$l/cm$^2$ on Transpore®-Tape) Australian/New Zealand Standard, 15/NZS 2604: 1993 (less than 10% transmission between 320 nm and 360 nm) is satisfied.

Example 17

Sunscreen Cream (W/O)

|   | Components | % by weight |
|---|---|---|
| Oil phase | Methoxy PEG-22/dodecyl glycol copolymer (Elfacos E 200 ®) | 3.00 |
|   | PEG-22/dodecyl glycol copolymer (Elfacos ST 37 ®) | 3.00 |
|   | Hydroxyoctacosanyl hydroxystearate (Elfacos C 26 ®) | 3.00 |
|   | Octyl stearate | 15.00 |
|   | Coco glycerides | 2.00 |
|   | Mineral oil | 3.00 |
|   | Phenoxyethanol & parabens | 0.70 |
|   | Compound of the formula (104) | 3.50 |
|   | 4-Methylbenzylidenecamphor | 4.00 |
|   | Tocopheryl acetate | 1.00 |
|   | Dimethicone | 0.20 |
| Aqueous phase | Deionized water | 56.80 |
|   | Magnesium sulfate (MgSO$_4$ × 7 H$_2$O) | 0.80 |
|   | Propylene glycol | 4.00 |

Preparation Procedure:

Phases A and B are heated separately to 80° C. and then mixed with gentle stirring. C is added to the mixture of A and B and then vigorously homogenized. The homogenate is allowed to cool to room temperature with gentle stirring. If necessary, the pH is adjusted by adding D.

SPF (in vitro)=12.0 (Optometrics SPF 290 Analyser, 2 $\mu$l/cm$^2$ on Transpore®-Tape) Australian/New Zealand Standard, 15/NZS 2604: 1993 (less than 10% transmission between 320 nm and 360 nm) is satisfied.

Example 18

Sunscreen Cream

|   | Components | % by weight |
|---|---|---|
| 1 | Deionized water | ad 100 |
| 2 | Titanium dioxide (and) isopropyl myristate | 6.25 |
| 3 | Phenoxyethanol & parabens | 0.50 |
| 4 | Salcare SC91 | 2.50 |
| 5 | Glycerol | 2.00 |
| 6 | Compound of the formula (104) | 0.70 |
| 7 | Isopropyl palmitate | 5.00 |
| 8 | Caprylic/capric triglyceride | 2.50 |
| 9 | Propylene glycol | 1.00 |
| 10 | Methylene bis(benzotriazolyl) (tetramethylbutyl)phenol (50% suspension) | 6.00 |

Preparation Procedure:

Substances (2) to (5) are added to water (1) in the given sequence with vigorous stirring. The solution of (6) in a mixture with (7) and (8) is then added with moderate stirring. Likewise with stirring, (9) and (10) are added. Continue stirring until the composition is homogeneous.

Australian/New Zealand Standard, 15/NZS 2604: 1993 (less than 10% transmission between 320 nm and 360 nm) is satisfied.

What is claimed is:

1. A compound of the formula

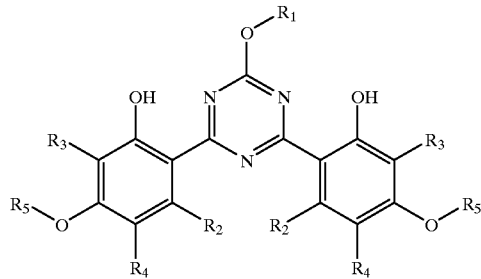
(1)

in which

R$_1$ is C$_6$–C$_{30}$alkyl; C$_2$–C$_{30}$alkenyl; unsubstituted or C$_1$–C$_5$alkyl-mono- or polysubstituted C$_5$–C$_{12}$cycloalkyl, C$_1$–C$_5$alkoxy-C$_1$–C$_{12}$alkyl; amino-C$_1$–C$_{12}$alkyl; C$_1$–C$_5$monoalkylamino-C$_1$–C$_{12}$alkyl; C$_1$–C$_5$dialkylamino-C$_1$–C$_{12}$alkyl; a radical of the formula

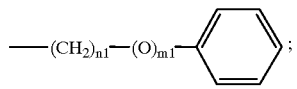
(1a)

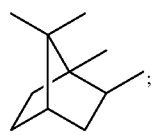
(1b)

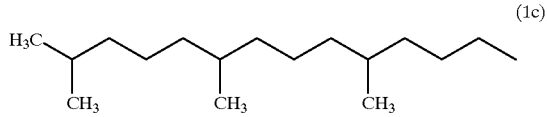
(1c)

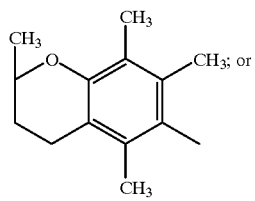
(1d)

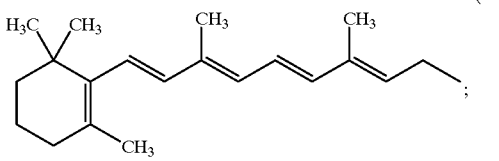

R$_2$, R$_3$ and R$_4$, independently of one another, are hydrogen, hydroxyl, C$_1$–C$_{30}$alkyl, C$_1$–C$_{30}$alkenyl, R$_5$ is hydrogen;

m$_1$ is 0 or 1; and n$_1$ is 1 to 5.

2. A compound according to claim 1, wherein R$_1$ is a 2-decylhexadecyl radical.

3. A compound according to claim 1, wherein R$_1$ is an isooctadecyl radical.

4. A compound according to claim 1, wherein R$_1$ is an n-octadecyl radical.

5. A compound according to claim 1, wherein R$_1$ is a 2-hexyldecyl radical.

6. A compound according to claim 1, wherein R$_1$ is a 2-ethylhexyl radical.

* * * * *